United States Patent [19]

Sherman et al.

[11] Patent Number: 4,612,286
[45] Date of Patent: * Sep. 16, 1986

[54] ACID HYDROLYSIS OF BIOMASS FOR ALCOHOL PRODUCTION

[75] Inventors: Michael I. Sherman; Carl L. Elmore, both of Glens Falls, N.Y.

[73] Assignee: Kamyr, Inc., Glens Falls, N.Y.

[*] Notice: The portion of the term of this patent subsequent to Mar. 13, 2001 has been disclaimed.

[21] Appl. No.: 633,350

[22] Filed: Jul. 23, 1984

Related U.S. Application Data

[63] Continuation-in-part of Ser. No. 335,517, Dec. 29, 1981, abandoned, which is a continuation-in-part of Ser. No. 122,270, Feb. 19, 1980, abandoned.

[30] Foreign Application Priority Data

Feb. 13, 1981 [CA] Canada .................. 370908

[51] Int. Cl.$^4$ .......... C12P 7/04; C13K 1/02; C02F 3/00; D21C 11/00
[52] U.S. Cl. ............... 435/157; 435/158; 435/160; 435/161; 435/163; 435/164; 435/165; 435/251; 435/252; 435/255; 435/911; 127/37; 210/601; 210/203; 162/14; 162/16
[58] Field of Search ........... 435/161, 163, 164, 165, 435/251, 252, 255, 158, 160, 832, 929, 157, 911; 426/14, 48; 127/37, 1; 210/77, 601, 203; 162/16, 14

[56] References Cited

U.S. PATENT DOCUMENTS

| | | | |
|---|---|---|---|
| 930,274 | 8/1909 | Doughty | 435/165 |
| 1,253,854 | 1/1918 | Marchand et al. | 435/164 |
| 1,261,328 | 4/1918 | Wagner | 260/124 R |
| 1,269,287 | 6/1918 | Lackman | 435/164 |
| 1,363,540 | 12/1919 | Moore | 435/165 |
| 2,086,701 | 7/1937 | Dreyfus | 435/163 |
| 2,295,150 | 9/1942 | Arroyo | 435/161 |
| 2,371,208 | 3/1945 | Alzola | 435/162 |
| 2,429,143 | 10/1947 | Tomlinson | 435/165 |
| 2,481,263 | 9/1949 | Tsuchiya et al. | 435/160 |
| 2,964,449 | 12/1960 | Thomsen | 435/150 |
| 3,212,932 | 10/1965 | Hess et al. | 127/37 |
| 3,372,087 | 3/1968 | Richter | 162/251 |
| 4,023,982 | 5/1977 | Knauth | 127/37 |
| 4,064,015 | 12/1977 | Nyiri et al. | 435/3 |
| 4,070,232 | 1/1978 | Funk | 162/16 |
| 4,076,623 | 2/1978 | Golston | 210/77 |
| 4,093,516 | 6/1978 | Lang | 435/165 |
| 4,124,440 | 11/1978 | Sherman | 162/246 |
| 4,172,037 | 10/1979 | Golston | 210/315 |
| 4,174,997 | 11/1979 | Richter | 162/19 |
| 4,201,596 | 5/1980 | Church et al. | 435/163 |
| 4,359,534 | 11/1982 | Kurtzman et al. | 435/161 |
| 4,425,433 | 1/1984 | Neves | 435/163 |
| 4,436,586 | 3/1984 | Elmore | 162/19 |
| 4,477,569 | 10/1984 | Schneider et al. | 435/161 |
| 4,520,105 | 5/1985 | Sinner et al. | 435/161 |
| 4,529,699 | 7/1985 | Gerez et al. | 435/165 |

OTHER PUBLICATIONS

Mann, William C., "Biomass Refinery Turns Crop Wastes Into Fuel," Popular Science, Apr. 1979, vol. 214, No. 4.

Lee et al. "Hemicellulose Hydrolysis and Fermentation of Resulting Pentoses to Ethanol", Tappi Journal, May. 1983, pp. 102–107.

Deverell, "Ethanol Production from Wood Hydrolysates Using Pachysolen Tannophilus", Biotechnology Letters, vol. 5, No. 7, 1983, pp. 475–480.

Primary Examiner—Thomas G. Wiseman
Assistant Examiner—Elizabeth C. Weimar
Attorney, Agent, or Firm—Nixon & Vanderhye

[57] ABSTRACT

A method of treating biomass having fermentable material is provided utilizing acid hydrolysis in a countercurrent diffusion treatment structure. By practicing the invention acid usage is minimized, pentose concentration in the hydrolysate solution is maximized, and ethanol, butanol, butanediol, and the alcohols can be produced without the input of any external energy whatsoever into the production method. Biomass is particlized and slurried, and then is continuously subjected to acid hydrolysis at temperature, acid concentration, and residence time conditions sufficient to effect hydrolysis of the hemicellulose in the biomass to effect separation of pentose and hexose sugars into a hydrolysate having insufficient furfural to substantially inhibit fermentation microorganism growth, while not substantially hydrolyzing the cellulose in the biomass. Fermentation of the pentose and hexose sugars in the hydrolysate may then be effected, and alcohol produced from the fermented pentose and hexose sugars utilizing conventional techniques. Hydrolysis is practiced in an upright diffusion vessel with countercurrent flow, the acid concentration being about 2 to 10%, the temperature in the vessel being about 120° C. or less, the residence time of the biomass in the vessel being about 1 to 3 hours, the biomass solids to liquid ratio being about 20/100 to 40/100 on a volume basis, and the particle size of the biomass being about 1–4 mm.

20 Claims, 5 Drawing Figures

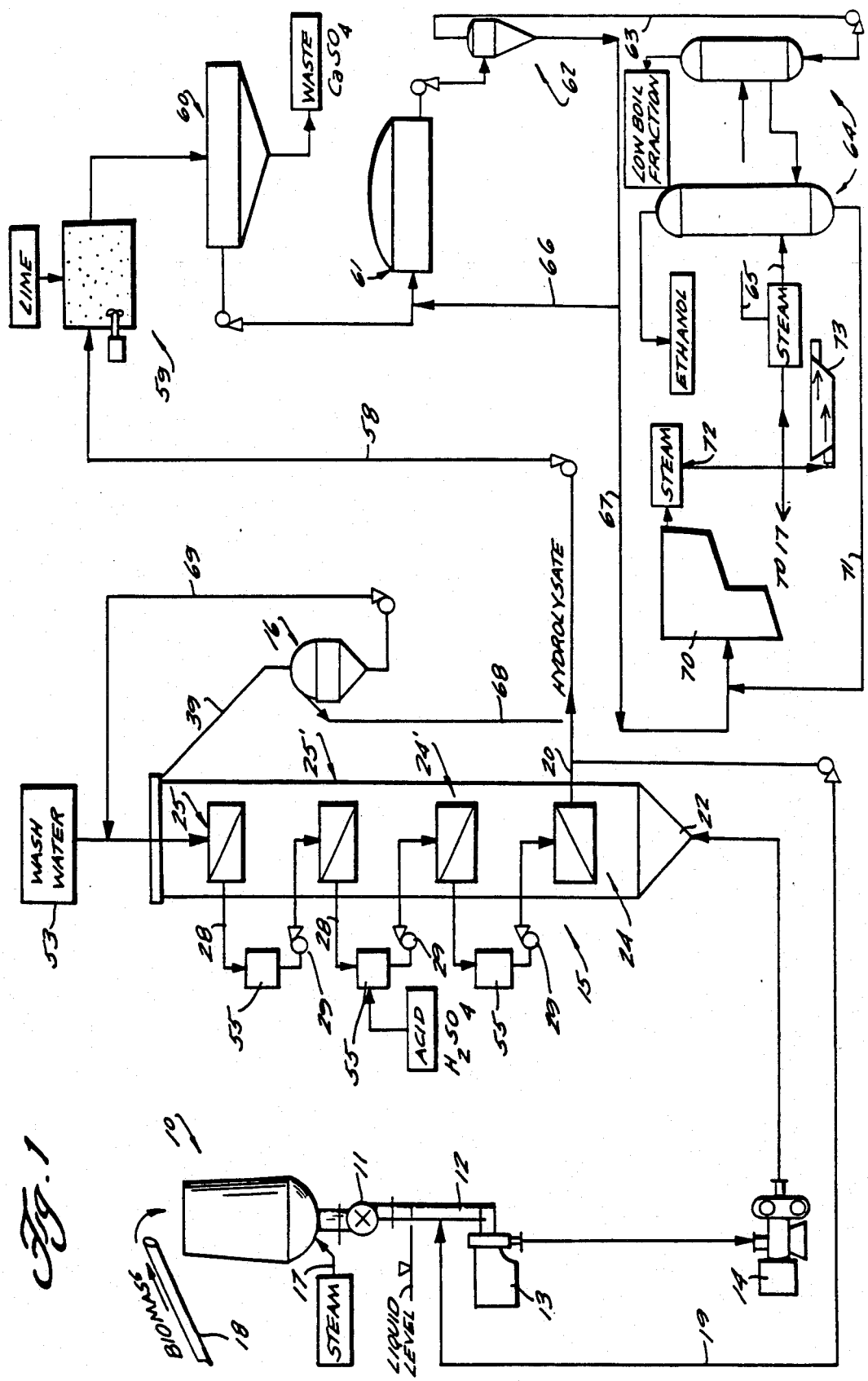

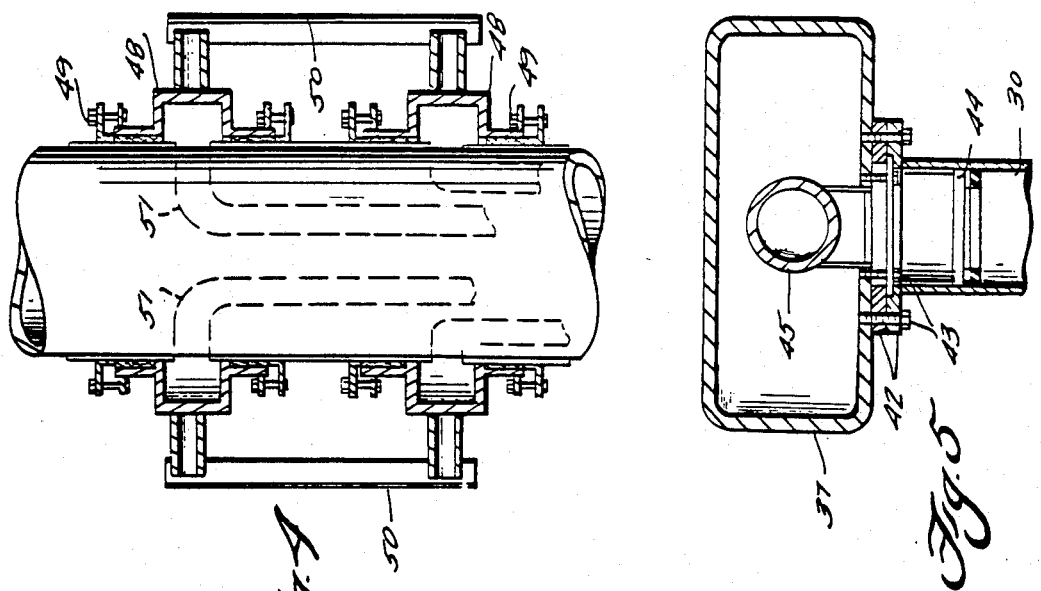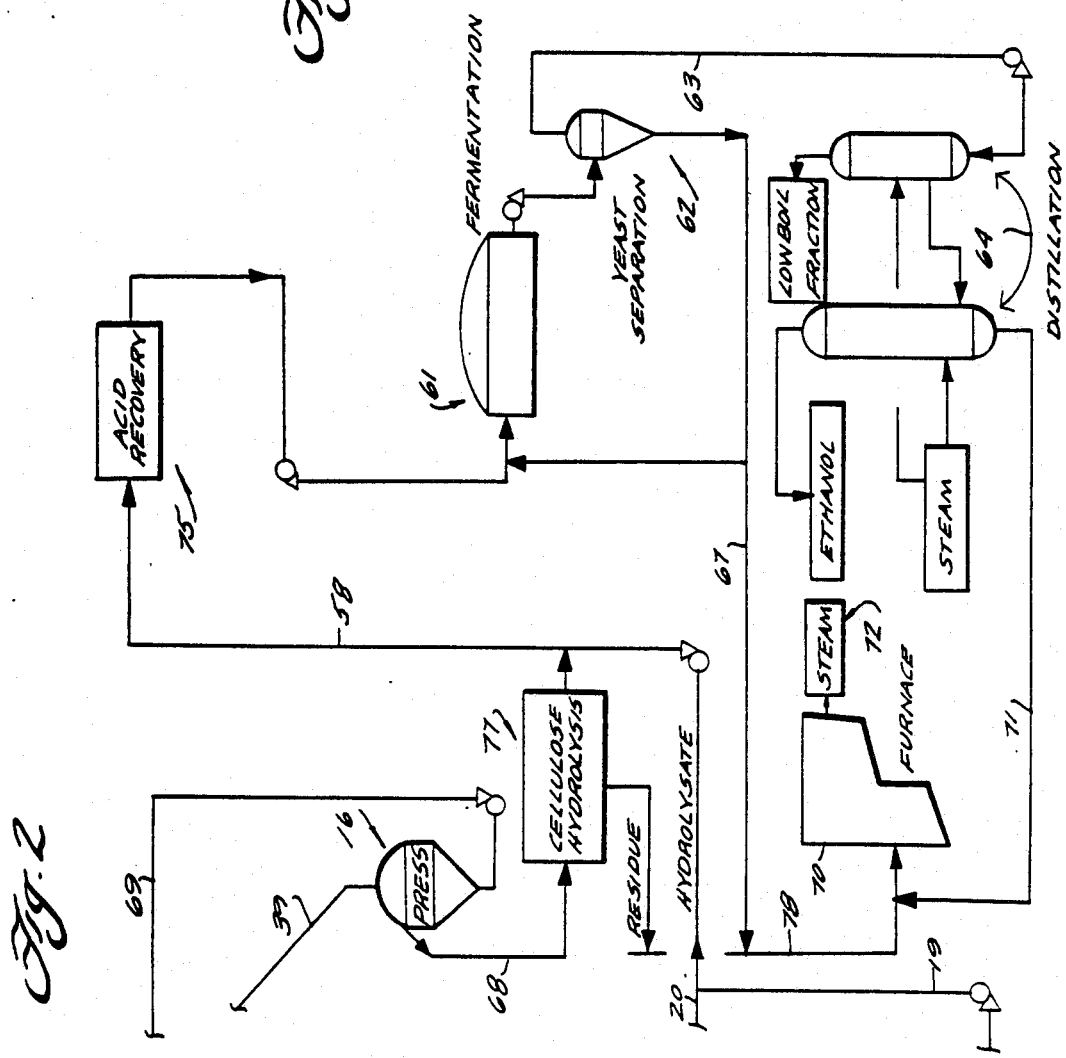

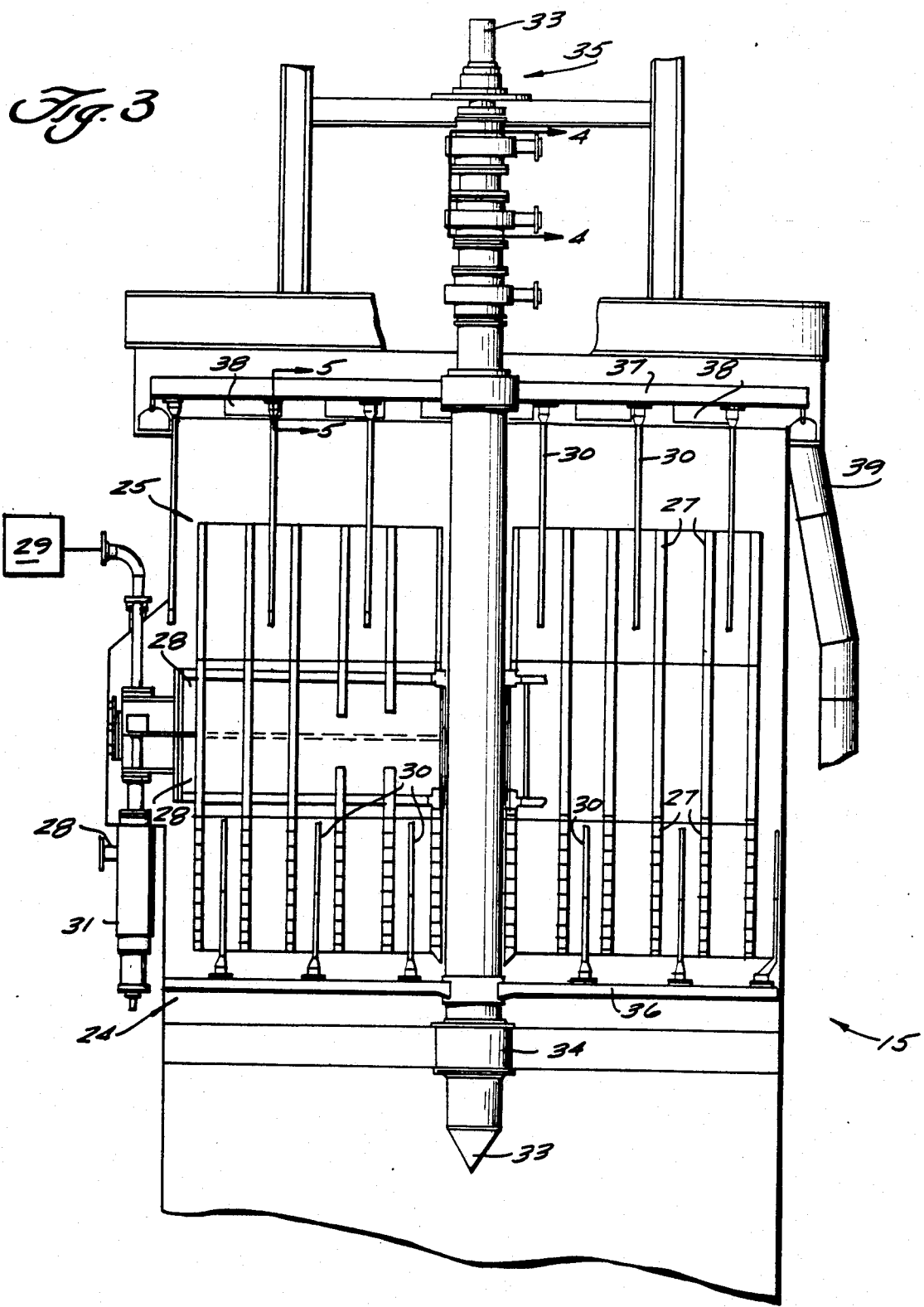

ACID HYDROLYSIS OF BIOMASS FOR ALCOHOL PRODUCTION

CROSS REFERENCE TO RELATED APPLICATION

This application is a continuation-in-part of application Ser. No. 335,517 filed Dec. 29, 1981, now abandoned, which in turn is a continuation-in-part of application Ser. No. 122,270 filed Feb. 19, 1980, now abandoned.

BACKGROUND AND SUMMARY OF THE INVENTION

Throughout the world there is an increasing demand for premium fuels utilizable in transportation, with emphasis on fuels to supplement or supplant refined petroleum fuels. Alcohols represent the presently most promising of such premium fuels since alcohols can be produced effectively from renewable resources, biomass, particularly forest and farm wastes. In order to gain widespread usage and acceptance as a fuel for transportation needs, however, alcohol must be produceable at facilities that are net energy producers.

Biomass contains two basic constituents, carbohydrates and lignin. The carbohydrate content of the biomass consists of cellulose and hemicellulose, both polysaccharides. Both cellulose and hemicellulose may be converted to simple sugars, particularly hexose (including glucose, fructose, mannose and galactose) and pentose (including xylose and arabinose) sugars. The hexose sugars are conventionally fermented to form ethanol, and the pentose sugars are now fermentable utilizing a variety of commercially available microorganism strains, including (but not limited to) the yeast *Pachysolen tannophilus* NRRL Y-2460, the yeast *Candida tropicalis* ATCC 1369, Fursarium strains of fungus developed by Argone National Laboratory, and *Bacillus Macerans* developed by The University of California at Berkley, and Lawrence Berkley Laboratory. Ethanol, butanol, 2,3-butanediol, are typical alcohols produced. All are practical and versatile alcohols for transportation usages since high percentages can be mixed with gasoline without significant engine modifications, and they have relatively few corrosive effects on vehicle fuel systems.

Conventional techniques for producing alcohol center around the breakdown of cellulose into hexose and pentose sugars with subsequent fermentation of the hexose sugars. It is questionable, however, if there really is a net production of energy when cellulose hydrolysis is practiced since large amounts of energy are needed to maintain the high temperature and superatmospheric pressures needed for cellulose hydrolysis and since simple sugar solutions contain suspended lignin after cellulose hydrolysis, separation of such suspended lignin being very difficult and requiring expensive and energy intensive equipment.

According to the present invention, fuel alcohols can be produced from biomass containing carbohydrate and lignin with a net energy production. That is, according to the method of the present invention alcohol can be produced from biomass without the addition of energy from any external source, the introduced biomass itself providing both the raw material for the ethanol and the energy for all process steps. In fact, according to the present invention, depending upon the particular operational steps and parameters, more energy than is necessary for all of the process steps may be produced, and may be sold either as steam or electricity.

According to one aspect of the method of the present invention, alcohol is produced from biomass containing carbohydrate and lignin by particlizing and slurrying the biomass and then continuously subjecting the biomass to acid hydrolysis. The acid hydrolysis is performed at temperature, acid concentration, and residence time conditions sufficient to effect hydrolysis of the hemicellulose in the biomass to effect separation of pentose and hexose sugars therefrom into a hydrolysate having insufficient furfural to substantially inhibit fermentation microorganism growth, while not substantially hydrolyzing the cellulose in the biomass. Then fermentation of the pentose and hexose sugars in the hydrolysate is effected—such as by exposing them, under proper environmental conditions, to the yeast *Pachysolen tannophilus* NRRL Y-2460, Fursarium strains of fungus, and *Bacillus Macerans*, or the like—and then alcohol is produced from the fermented pentose and hexose sugars through normal processing (e.g. distillation]. By directing the hydrolysis toward hemicellulose breakdown, while not being concerned with cellulose breakdown, furfural production is minimized, as is energy usage, and the remaining biomass (including lignin and cellulose) remaining after acid hydrolysis of the hemicellulose can be burned to produce energy for all of the process steps, as well as additional energy for other purposes. It is necessary to minimize production of inhibitors, such as furfural, since small concentrations of some inhibitors can adversely affect the growth rate, or kill, the fermentation microorganisms.

The acid hydrolysis according to the present invention preferably is practiced with an acid concentration of about 2 to 10% by volume (preferably sulfuric acid), and the hydrolysis temperature is about 120° C. or less. The residence time in the acid hydrolysis treatment is about 1 to 3 hours, and the treated biomass slurry has a biomass solids to liquid ratio of about 20/100 to 40/100 on a volume basis. The particle size of the biomass is about 1–4 mm.

Acid hydrolysis of biomass is practiced according to the present invention utilizing an upright vessel having a plurality of sets of apparatus, each apparatus set including a plurality of concentric non-rotatable screen members each having an apertured face and having a conduit leading away from the face to an area remote from the screen members; a plurality of vertically extending spray tubes disposed between the screen members; and means for moving the screen members alternately upwardly and downwardly. The apparatus sets are spaced vertically in the vessel and conduits extend from the screen members in an apparatus set so that they are operatively connected to the spray tubes in the next lower apparatus set. The conduits from the lowermost apparatus set lead exteriorly of the vessel to a further remote treatment point. Apparatus suitable for practicing acid hydrolysis according to the invention may be practiced utilizing apparatus such as shown in U.S. Pat. Nos. 3,372,087 or 4,172,037, the disclosures of which are hereby incorporated by reference herein. The method comprises the steps of continuously: Particlizing and slurrying the biomass. Flowing the slurry upwardly in the vessel past the apparatus sets. Moving the screen members of each set upwardly and downwardly, preferably being moved upwardly at a first velocity about equal to the velocity of the upwardly flowing slurry in the vessel and downwardly at a velocity much greater than the first velocity. Introducing hot washing liquid into the spray tubes of the uppermost apparatus set. Passing withdrawn liquid from each apparatus set screen members to the next lowermost apparatus set spray tubes. Introducing acid into the withdrawn liquid between one of the apparatus set screen members and the next lowermost set spray tubes. Withdrawing as hydrolysate the liquid withdrawn from the lowermost apparatus set screen members, and passing it on to a further remote treatment point; and withdrawing the biomass slurry from the top of the vessel and dewatering it.

By practicing the present invention a higher solids to liquids ratio can be utilized than is conventional, resulting in low acid usage and minimized energy expenditure for pumping and the like, and the pentose concentration in the hydrolysate is maximized.

According to another aspect of the present invention, a method of treating biomass having fermentable material is provided. The method comprises the steps of: Particlizing the biomass. Feeding the biomass into a surge bin, and steaming the biomass in the surge bin. Controlling the rate of feed of biomass from the surge bin to a conduit in which the biomass is slurried, and slurrying the biomass in the conduit. Refining the slurried biomass to effect reduction of the particle size thereof (preferably to about 1–4 mm.) and pumping the slurried, refined biomass to an upright acid hydrolysis vessel. Continuously effecting acid hydrolysis of the biomass in the vessel at a temperature of about 120° C. or less to provide a hydrolysate. Passing a first portion of the hydrolysate to an ultimate destination for fermentation thereof, and passing a second portion of the hydrolysate to the slurrying conduit to effect slurrying of the biomass. Effecting washing of the biomass in the vessel after acid hydrolysis thereof by introducing a stream of hot wash water into a top portion of the vessel. Withdrawing hydrolyzed and washed biomass from the top of the vessel and effecting dewatering thereof; and passing the water from the dewatering of the biomass to the stream of wash water introduced into the vessel.

The hydrolysate preferably is acted upon by neutralizing it with lime, clarifying it, and then passing it to a conventional fermentation vessel. After fermentation, the "beer" is passed on to a yeast separation stage and then ultimately to conventional distillation towers where ethanol, butanol, 2,3-butanediol, and/or other alcohols, are produced. After dewatering the biomass is passed to a furnace, along with products from the yeast separation, to produce steam. The volume of steam produced is sufficient to supply the steam necessary for the distillation towers, for steaming of the biomass in the surge bin, for heating the wash water, and for running all necessary pumps, mixers, and the like. Additionally, there should be sufficient energy left over so that the entire facility is a net energy producer, producing steam or electricity in addition to the alcohol, without the introduction of energy from an external source (aside from the biomass itself).

Alternatively, instead of burning the biomass after dewatering, it may be passed to a cellulose hydrolysis stage wherein severe hydrolysis is practiced. The residue remaining from that stage may be burned as described above. Hydrolysate produced from either or both of the hemicellulose and/or cellulose hydrolysis stages may be subjected to acid recovery instead of neutralization, utilizing conventional techniques, before fermentation.

It is the primary object of the present invention to provide an efficient method of acid hydrolysis of biomass, primary for ultimate butanol, 2,3-butanediol, ethanol and like alcohol production. This and other objects of the invention will become clear from an inspection of the detailed description of the invention, and from the appended claims.

BRIEF DESCRIPTION OF THE DRAWINGS

FIG. 1 is a schematic view of a complete process for producing alcohol from biomass utilizing the teachings of the present invention;

FIG. 2 is a partial schematic view corresponding to FIG. 1 but showing a modification of the hydrolysate and hemicellulose hydrolyzed biomass treatment steps of the FIG. 1 embodiment;

FIG. 3 is a view partly in cross-section and partly in elevation of a portion of an exemplary hydrolysis vessel for practicing the present invention; and FIGS. 4 and 5 are detailed sectional views taken along lines 4—4 and 5—5 respectively of FIG. 3.

DETAILED DESCRIPTION OF THE DRAWINGS

Exemplary apparatus that may be utilized according to the method of the present invention for producing alcohol is illustrated schematically in FIG. 1. The basic components include a surge bin 10, a rate feeder 11, a conduit 12 in which a liquid level L is maintained, a refiner 13, a high density pump 14, a hydrolysis vessel 15, and a dewatering press 16. The surge bin 10 is conventional and steaming from source 17 may be effected directly in the surge bin 10, such as shown in U.S. Pat. No. 4,124,440, the disclosure of which is hereby incorporated by reference herein. The rate feeder 11, refiner 13, and high density pump 14 are also conventional. The refiner preferably has the plates thereof designed and spaced so that it refines particles to a size of about 1–4 mm.

Biomass containing carbohydrate and lignin, such as farm or forest wastes including cornstalks, bagasse, wood, etcetera, is first coarsely particlized and then introduced by conveyor 18 into surge bin 10, wherein steam from line 17 is added, the bin 10 being equipped with a vibrator to prevent bridging of the downward flowing coarse biomass particles. At this point the particles have a size and range of about 0.5 to 2.0 inches. The particlized biomass then passes through the vane-type rate feeder 11 into the conduit 12 in which it is slurried. Liquid to effect slurrying is preferably provided from conduit 19 which is connected to hydrolysate outlet 20 from the hydrolysis vessel 15. The particles are slurried so that the slurry has a biomass solids to liquids ratio of about 20/100 to 40/100 on a volume basis. The slurry passes to the conventional refiner 13, such as used in pulp production plants, wherein the particle size is reduced to a range of about 1–4 mm, and the slurry is then fed by high density pump 14 to the bottom inlet 22 of the hydrolysis vessel.

A preferred hydrolysis vessel 15 according to the present invention—which vessel can effectively practice hydrolysis on slurrys with a high solids to liquid ratio with resulting low acid and energy usage, and which can achieve high pentose concentration in the hydrolysate—comprises a countercurrent diffusion type vessel. Examples of such a vessel are provided in U.S. Pat. Nos. 3,372,087, 4,076,623, and 4,172,037, and in copending application Ser. No. 34,928 filed Apr. 25, 1979, the disclosures of each of which are hereby incorporated by reference herein. FIGS. 3 through 5 provide detailed drawings of a representative exemplary such countercurrent diffusion vessel 15.

The vessel 15 is upright and includes a plurality of sets, (e.g. 24 and 25 in FIG. 3) of apparatus, each set vertically spaced from the other. Each set (e.g. 24, 25) includes a plurality of concentric non-rotatable screen members 27 each having an apertured face and a conduit 28, connected to a suction source (e.g. pump) 29 or the like leading away from the apertured face to an area remote from the screen members 27. A plurality of vertically extending rotatable spray tubes 30 are associated with each apparatus set (e.g. 24, 25), the tubes 30 disposed between screen members 27, and means 31 are provided for alternately upwardly and downwardly moving the screen members 27 (and in some cases the spray tubes 30) of each apparatus set, the means 31 preferably effecting upward movemennt of the screen members 27 at a first velocity about equal to the velocity of the upwardly flowing slurry in the vessel 15, and the downward movement being at a velocity greatly in excess of the first velocity. A central shaft 33 is provided in the vessel, mounted by a bearing 34 within the vessel 15 and a thrust bearing 35 atop the vessel 15. A suitable power source is provided for effecting rotation of the shaft 34, and the spray tubes 30 are operatively attached to the shaft 34 by hollow arms 36, 37 (see FIG. 3). The top arms 37 also include a conventional rotatable scraper having blades 38, which serves to discharge the biomass slurry that ultimately flows to the top of the vessel 15 out the biomass discharge conduit 29.

FIG. 5 shows a detailed cross-sectional view of the fluid interconnection between a spray tube 30 and the arm 37, orifice plates 42, a cap screw 43, and a check valve 44 being provided between the spray tube 30 and an interior right-angle bent tube 45 for directing liquid within the arm 37 to the spray tube 30.

FIG. 4 shows details of a liquid input pack box surrounding the central shaft 33 at a location above the top of the vessel 10. A pack box 48 is mounted by a retaining nut 49 or the like to a pack box support 50, and a conduit or conduits 51 disposed interiorly of the central shaft 33 communicate with the pack box 48 to provide liquid flow to the spray tube arms 36, 37, each pack box 48 and conduits 51 associated therewith providing liquid flow to a different set of spray tubes 30.

One suitable form that the vessel 15 may take is illustrated schematically in FIG. 1 wherein four apparatus sets are provided, denoted sets 24, 24', 25, and 25'. The sets 24, 24' introduce an acid solution through the spray tubes 30 and effect acid hydrolysis, while the sets 25, 25' effect washing of the biomass. A source 53 of hot wash water supplies liquid for the washing sets 25, 25'. In such an arrangement, the conduit 28 leading from each set of screen members 27 leads to the spray tubes 30 of the next lowermost apparatus set. The conduit 28 from the screen members 27 of the lowermost set 24 leads to the hydrolysate outlet 20, which carries hydrolysate to subsequent remote points for further treatment for ultimate ethanol production. Intermediate containers 55 are provided in each fluid circuit with a pump 29 from a conduit 28 for heating, filtering, storing, or otherwise operating on the withdrawn liquid, and acid (e.g. sulfuric acid) is introduced at a vessel 55 in the liquid flow to the spray tubes 30 of the topmost hydrolysis set 24', as indicated in FIG. 1. Acid is introduced so that the acid concentration in the hydrolysis portion of the vessel 15 is about 2 to 10% by volume, and temperature and pressure conditions are maintained in the system so that the temperature in the vessel 15 is at about 120° C. or less so that the hemicellulose dissolution takes place at or slightly above atmospheric pressure (hydrolysis at 120° C. represents an operating pressure of approximately 15 psig). The residence time in the hydrolysis portion of the vessel 15 is about 1 to 3 hours, while the residence time in the washing portions of the vessel 15 is about 10 to 20 minutes, the washing diffusing hydrolysate from the unreacted biomass with hot water.

By practicing acid hydrolysis according to the present invention, the hemicellulose in the biomass is hydrolyzed to effect separation of pentose and hexose sugars therefrom, while the cellulose in the biomass is not substantially hydrolyzed. The hydrolysate withdrawn through the outlet 20 has insufficient furfural content to substantially inhibit fermentation microorganism growth. When subsequent fermentation is practiced, for instance, utilizing *Pachysolen tannophilus* NRRL Y-2460 yeast the concentration of inhibitors in the hydrolysate are minimized.

The following table indicates the results of actual tests performed utilizing *Pachysolen tannophilus* NNRL Y-2460 utilizng various hydrolysate, and a test utilizing *Candida tropicalis* ATCC 1369. The hydrolysate was supplemented with nutrients required for growth of the yeast except xylose. Other microorganisms also could be utilized such as AU-1-d3 strain microorganisms located by Auburn University, Fursarium strains of fungus, and *Bacillus macerans*.

TABLE I

| Organism | Initial xylose concentration, % | Time | Ethanol Concentration, % | Yield % |
| --- | --- | --- | --- | --- |
| *Candida tropicalis* ATCC 1369 | 7.5 | — | 0.55 | 7.3 |
| *Pachysolen tannophilus* NRRL Y-2460 | 5 | 100 hr. | 1.7 | 34 |
| *Pachysolen tannophilus* NRRL Y-2460 Wheat Straw Hydrolyzate | 4.3 | 6 days | 0.72 | 17 |
| *Pachysolen tannophilus* NRRL Y-2460 Oak wood hydrolyzate | 6 | 7 days | 1.0 | 20 |

In actual production of alcohol by fermentation, care must be taken to minimize inhibitors toxic to the microorganisms. Typical inhibitors include sugar decomposition products (e.g. acetic acid, furfural, and hydrorymethylfurfural), and low-molecular-weight phenols derived from lignin and wood extractives (such as resin acids, tannic acid, and terpenes). For example, since some 70% of the xylose residues of typical hardwood contain an O-acetyl group, acetic acid will be formed upon acid hydrolysis of wood. A concentration of 0.5% acetic acid in minimal medium completely inhibits growth of *P. tannophilus* NRRL Y-2460 at pH 3.0, 4.2, and 5.2, whereas 0.05% and 0.10% concentrations stimulate growth at the pH values (FIG. 5). Growth is stimulated also by 0.25% acetic acid at pH 4.2 and 5.2, but inhibition occurs at pH 3.0. These results suggest that fermentation of wood hydrolyzates with *P. tannophilus* may require a high pH than the optimum pH 2.5 reported for maximum ethanol production from xylose in minimal medium.

After being withdrawn through outlet 20 from the vessel 15, the hydrolysate passes through line 58 to subsequent treatment steps, preferably eventually being passed to a fermentation stage wherein the pentose and hexose sugars in the hydrolysate are fermented, and subsequently an alcohol production stage wherein ethanol butanol, butanediol and/or other alcohols are produced from the fermented pentose and hexose sugars. In the modification illustrated in FIG. 1, hydrolysate from line 58 passes to a conventional mixing tank 59 wherein it is neutralized with lime, and subsequently passes to a conventional clarification apparatus 60 and then to a conventional fermenter 61. In the fermenter 61 suitable microorganisms under appropriate environmental conditions act upon both the pentose and hexose sugars to effect fermentation thereof. The withdrawn "beer" from the fermenter 61 passes through a conventional yeast apparatus 62 through line 63 to distillation tower 64, steam being provided through line 65 for the distillation. A portion of the separated material from the yeast separation station 62 is passed through line 66 back to the fermenter 61, while another portion is passed through line 67 to the dicharge line 68 from press 16.

In the modification illustrated in FIG. 1, the hemicellulose hydrolyzed biomass discharged through the biomass discharge conduit 39 from vessel i5 is dewatered by conventional press 16, the water removed from the biomass being separated through line 69 to be fed with water from the source 53 to the spray tubes of the apparatus set 25 in vessel 15. The solids from the press 16 pass through line 68 to a furnace 70 or the like, where they are burned along with products supplied through lines 67 and 71 from the yeast separation apparatus 62 and the distillation apparatus 64, respectively. The biomass contains cellulose and lignin and is burned to produce steam, and steam production being illustrated in FIG. 1 at 72. The production of steam is sufficient such that from source 72 steam may be supplied to conduit 17 for steaming the biomass in surge bin 10, to distillation apparatus 64 through conduit 65, and to a turbine 73 or the like for the production of electricity for powering all of the pumps, presses, refiners, conveyors, or the like in the system. Additionally, sufficient energy will be left over so that the entire process will have a net production of steam or electricity that can be sold.

A modification of the FIG. 1 embodiment for the subsequent treatment of the hydrolysate and hemicellulose hydrolyzed biomass is illustrated in FIG. 2. In this embodiment, hydrolysate passing through line 58 goes to an acid recovery stage where the introduced acid is at least partially recovered (e.g. through electrodialysis), and then is subsequently ultimately passed to the fermenting and distillation appartus 61, 64, etcetera. The hemicellulose hydrolyzed biomass, instead of passing through line 68 directly to the furnace 70, passes instead to a conventional severe hydrolysis apparatus 77 wherein the cellulose is hydrolyzed, and the residue passes from apparatus 77 through line 78 to the furnace 70. In this embodiment insufficient steam is produced at station 72 by the furnace 70 to supply all of the power needs for the process (although alcohol production is increased) so that energy must be supplied from an external source.

In a typical treatment method according to the present invention, biomass is coarsely partclized to a size range of 0.5–2.0 inches and fed by conveyor 18 to surge bin 10 wherein it is steamed, slurried in conduit 12 so that the solids/liquid ratio is about 20/100–40/100, refined by refiner 13 to a particle size of about 1–4 mm., and pumped to an upright acid hydrolysis vessel 15. The slurry is flowed upwardly in the vessel 15 past the apparatus sets 24, 24', 25', and 25 in succession. Hot washing liquid is introduced into the spray tubes 30 of the upper most apparatus set 25, and withdrawn liquid from each apparatus set screen members 27 is passed to the next lowermost apparatus set spray tubes (e.g. from screen members 27 of set 25 to tubes 30 of set 25'). Sulfuric acid is introduced into the withdrawn liquid at container 55 between the apparatus sets 25' and 24' to achieve an acid concentration of about 2 to 10%, while the temperature within vessel 15 is maintained at about 120° C. or less.

The liquid withdrawn from the lowermost apparatus set 24 screen members 27 is withdrawn as hydrolysate and passed into conduit 58, while the biomass slurry is moved by scraper blades 38 into the conduit 39. A first portion of the hydrolysate, that in conduit 58, is passed to the further treatment stage for ultimate neutralization, acid recovery, or the like, and subsequent alcohol production, while a second portion of the hydrolysate is passed through line 19 to effect slurrying of the biomass in conduit 12. Washing of the biomass in vessel 51 utilizing apparatus sets 25, 25' is effected by introduced a stream of hot wash water from source 53 into the spray tubes 30 of the topmost apparatus set 25. The withdrawn biomass in conduit 39 is subjected to dewatering in press 16, and the water from the dewatering is passed through line 69 back to the stream of wash water into vessel 15 after combining with water from source 53.

It will thus be seen that according to the present invention an effective method has been provided for effecting acid hydrolysis and hemicellulose in biomass, primarily for subsequent ethanol production, the method being capable of effecting alcohol production from biomass without the introduction of any energy into the system from an external source. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and processes.

What is claimed is:

1. A method of producing fuel alcohol from biomass containing carbohydrate and lignin, comprising the steps of:
    (a) particlizing and slurrying the biomass;
    (b) continuously subjecting the biomass to acid hydrolysis at temperature, acid concentration, and residence time conditions sufficient to effect hydrolysis of the hemicellulose in the biomass to effect separation of pentose and hexose sugars therefrom into a hydrolysate having insufficient furfural to substantially inhibit fermentation microorganisms growth, while not substantially hydrolyzing the cellulose in said biomass by: establishing a flow of the slurried biomass in a first direction in a vessel; contacting the flowing slurry with a plurality of concentric non-rotatable screen members each having an apertured face and having a conduit leading away from the face to an area remote from said flow; introducing dilute acid into the slurry flow through a plurality of rotatable spray tubes extending parallel to the direction of said slurry and disposed between said screen members in a direction perpendicular to the direction of flow; removing hydrolysate from the flow by withdrawing liquid through the screen members and passing it through the conduit; and moving the screen members alternately generally in said direction of slurry flow and in a direction opposite said direction of slurry flow;

(c) effecting fermentation of the pentose and hexose sugars in said hydrolysate; and (d) producing fuel alcohol from the fermented pentose and hexose sugars.

2. A method as recited in claim 1 wherein step (b) is practiced by providing an acid concentration of about 2-10% by volume, and a hydrolysis temperature of about 120° C. or less to effect hydrolysis.

3. A method as recited in claims 2 wherein step (b) is further practiced by providing a residence time in the vessel of about 1-3 hours.

4. A method as recited in claim 2 wherein step (a) is practiced so that the biomass solids to liquid ratio is about 20/100 to 40/100 on a volume basis.

5. A method as recited in claim 1 comprising the further step of steaming the biomass before slurrying thereof.

6. A method as recited in claim 1 wherein step (b) is further practiced by providing two sets of screen members and spray tubes spaced along said direction of flow, providing a first grouping and comprising the further step of washing the biomass by providing two further sets of screen members and spray tubes, comprising a second grouping, spaced from the first grouping along the direction of flow, and introducing hot water into the flow through the second grouping spray tubes.

7. A method as recited in claim 6 wherein the vessel is upright and the direction of flow of the slurry is upwardly, with the second grouping vertically above the first grouping; and wherein the second grouping comprises first and second screen sets and spray tubes, and wherein the first grouping comprises third and fourth screen sets and spray tubes; and wherein said acid hydrolysis and washing steps are practiced by: introducing hot water into the first set spray tubes; withdrawing liquid from the first set screen members and introducing it into the second set spray tubes; withdrawing liquid from the second set screen members, adding hydrolyzing acid thereto, and introducing it into the third set spray tubes; withdrawing liquid from the third set screen members and introducing it into the fourth set spray tubes; and withdrawing hydrolysate from the fourth set screen members and passing it exteriorly of the vessel for ultimate fermentation.

8. A method as recited in claim 1 wherein the vessel is upright and the flow of the slurry is upwardly, and wherein a plurality of sets of screen members and spray tubes is provided, each set vertically spaced from the others, and wherein step (b) and a subsequent washing step are practiced by introducing liquid withdrawn from each set screen members into the next lower set spray tubes, with liquid withdrawn from the lowest set screen members passed exteriorly of the vessel to said subsequent fermentation step.

9. A method as recited in claim 1 wherein step (a) is accomplished by coarsely particlizing the biomass, then slurrying the biomass, and then finely particlizing the biomass to a final particle size of about 1-4 mm.

10. A method as recited in claim 1 comprising the further step of effecting water removal from the biomass after acid hydrolysis thereof, and then burning the biomass to provide at least sufficient energy for practicing steps (a)-(d), and for steaming the biomass before slurrying thereof.

11. A method as recited in claim 1 comprising the further step of subjecting the acid-hydrolyzed biomass to further hydrolysis to effect separation of the fermentable sugars from the cellulose component of the biomass.

12. A method as recited in claim 1 comprising the further step of effecting neutralization and clarification of the hydrolysate before subjecting it to fermentation.

13. A method as recited in claim 1 wherein step (b) is practiced utilizing sulfuric acid.

14. A method as recited in claim 1 wherein step (c) is practiced utilizing *Pachysolen tannophilus* NRRL Y-2460 yeast.

15. A method of effecting acid hydrolysis of biomass utilizing an upright vessel having a plurality of sets of apparatus, each apparatus set including a plurality of concentric non-rotatable screen members each having an apertured face and having a conduit leading away from the face to an area remote from the screen members, and a plurality of vertically extending rotatable spray tubes disposed between the screen members, and means for moving the screen members alternately upwardly and downwardly, the apparatus sets being vertically spaced in the vessel and the conduits extending from the screen members in an apparatus set being operatively connected to the spray tubes in the next lower apparatus set, and the conduits in the lowermost apparatus set leading exteriorly of the vessel to a further remote treatment point; said method comprising the steps of continuously:

particlizing and slurrying the biomass;
flowing the slurry upwardly in the vessel past the apparatus sets;
moving the screen members of each set upwardly and downwardly;
introducing hot washing liquid into the spray tubes of the uppermost apparatus set;
passing withdrawn liquid from each apparatus set screen members to the next lowermost apparatus set spray tubes;
introducing acid into the withdrawn liquid between one of the apparatus set screen members and the next lowermost set spray tubes;
withdrawing as hydrolysate the liquid withdrawn from the lowermost apparatus set screen members, and passing it on to a further remote treatment point; and
withdrawing the biomass slurry from the top of the vessel and dewatering it.

16. A method as recited in claim 15 wherein four apparatus sets are provided, and wherein said acid introducing step is practiced by introducing sulfuric acid into the liquid being introduced into the spray tubes of the second from the bottom apparatus set.

17. A method as recited in claim 15 wherein the screen members moving step is accomplished by moving the screen members upwardly at a first velocity about equal to the velocity of the upwardly flowing slurry in the vessel, and periodically moving the screen members downwardly at a velocity greatly in excess of said first velocity.

18. A method as recited in claim 15 comprising the further step of maintaining the temperature in the vessel at 120° C. or below, and wherein said passing step is practiced so that the residence time in the hydrolysis portion of the vessel is about 1–3 hours.

19. A method as recited in claim 15 wherein said slurrying and particlizing step is practiced so that the slurry has a solids to liquid ratio, by volume, of between 20/100 and 40/100, and the particles have a size of about 1–4 mm.

20. A method as recited in claim 18 wherein said slurrying and particlizing step is practiced so that the slurry has a solids to liquid ratio, by volume, of between 20/100 and 40/100, and the particles have a size of about 1–4 mm.

* * * * *